United States Patent [19]

Krulwich et al.

[11] Patent Number: 5,346,815

[45] Date of Patent: Sep. 13, 1994

[54] SODIUM ION BINDING PROTEINS

[75] Inventors: Terry A. Krulwich, New York, N.Y.; D. Mack Ivey, Fayetteville, Ark.

[73] Assignee: The Mount Sinai School of Medicine of the City University of New York, New York, N.Y.

[21] Appl. No.: 938,188

[22] Filed: Aug. 28, 1992

[51] Int. Cl.$^5$ .................. C12N 1/20; C12N 15/00; C07H 19/00; C07H 21/00
[52] U.S. Cl. ................. 435/69.1; 435/252.3; 435/320.1; 536/22.1; 536/23.4; 536/23.7
[58] Field of Search ............. 435/69.1, 252.3, 320.1; 536/22.1, 23.4, 23.7

[56] References Cited

PUBLICATIONS

Glover "Principle of Cloning DNA" *Gene Cloning* pp. 1–20 1984.
Green et al. "The Role of Antisois RNA ..." Ann Rev. Bioch. 55:569–97 1986.
Glover "Expression of Cloned DNAs in G. coli plasnode" *Gene Cloning* pp. 110–127 1984.
Aronson, P. S., 1985 "Kinetic Properties of the Plasma Membrane NA$^+$–H$^+$ Exchange" Ann. Rev. Physiol. 47:545–560.
Shull, G. E. et al., 1986, "Molecular Cloning of Three Distinct Forms of the Na$^+$, K$^+$–ATPase α–Subunit From Rat Brain" Biochemistry 25:8125–8132.
Krulwich, T. A. and Guffanti, A. A. 1989, "Alkalophillic Bacteria" Annu. Rev. Microbiol. 43:435–63.
Sardet, C. et al., 1989, "Molecular Cloning, Primary Structure, and Expression of the Human Growth Factor–Activatable Na$^+$/H$^+$ Antiporter" Cell 56:271–280.
Padan, E. et al., 1989, "Deletion of ant in *Escherichia coli* Reveals its Function in Adaptation to High Salinity and an Alternative Na$^+$/H$^+$ Antiporter System" J. Biological Chemistry 264:20297–20302.
Nicoll, D. A. et al., 1990, "Molecular Cloning and Functional Expression of the Cardiac Sarcolemmal Na$^+$–Ca$^+$ Exchanger" Science 250:562–565.
Ivey, D. M. et al., 1991, "Molecular Cloning and Sequencing of a Gene from Alkalphilic *Bacillus firmus* OF4 That Functionally Complements and *Escherichia coli* Strain Carrying a Deletion in the nhaA Na$^+$/H$^+$ Antiporter Gene" J. Biological Chemistry 266:23483–23489.

*Primary Examiner*—Robert A. Wax
*Assistant Examiner*—Hyosuk Kim
*Attorney, Agent, or Firm*—Pennie & Edmonds

[57] ABSTRACT

The present invention relates to the cloning and expression of a sodium ion binding protein. In particular, the invention relates to cloning and expression of a nhaS gene. The nhaS gene product, NhaS, is a protein characterized by binding to and sequestering sodium ion (Na$^+$). The invention further relates to functional fragments of a sodium ion binding protein, which fragments are characterized by their ability to bind to sodium ion. In a specific embodiment, the fragment is a fragment of NhaS. The gene encoding the sodium binding protein can be introduced into cells to produce desalination bioreactors. The gene encoding the sodium binding protein can also be introduced into plants as a transgene to produce plants that are resistant to sodium. The sodium binding protein itself may be used for treatments involving Na$^+$/K$^+$ ATPase disorders, e.g., in heart disease; the protein also may be introduced parenterally, preferably orally, to bind to and sequester dietary sodium.

11 Claims, 6 Drawing Sheets

```
AAACGTGGATAAAGCAAGTGGATTTGATGCAAGTAAGGATAAGGAGGGATGACCATGTTTAGCCGTC
                                                           M  F  S  R  L
                                                          Hhas>

TTATCTCAATTGTTAGTTAATCTTGTCTTTTACTTTGCTTACAAATATCCGTACCGTGTTATTAATGCAGTGCTCGGACGCCGTTGGCTGCTGGAAAGT
 I  S  I  V  S  L  I  L  S  F  Y  F  A  Y  K  Y  R  Y  R  V  I  N  A  V  L  G  R  R  W  L  R  K  V

GATTATTGGTTTTGCCGATGCAGATCCCCATGATGATCAGAGACCGTATGCTAGGATCCGTTCTCGCAGTCTAATCGACCTCAAAATGTGTAACAAACAAGAAAG
 I  I  G  F  A  M  Q  I  P  M  I  R  D  R  M  L  G  S  V  L  Q  S  N  R  P  Q  N  V  *

TCTGATGTTCACTTTAATGAAAGTAAAGTATGGCATCAGACTTTTTCGTATATATACATACTATAAGGCTTATTAATGTCCTAACCTTTAGAGCCCTTG

TTATACTATAAGGGATACGGAGGATTGTATCTTGAAAGTGAAGTGGAGTACCGATATGTTTTGATTTAGATAATACGTTATATAACCATGAGTATGCTTTTA

AGCGTGGCGATTAAACAATGTTACTATACAAAACTTCAGCAATGGAAGATATCCGTTGATCACGGCTCCTCCATTTGAAGCATGGTTTACTACACATTTAAATA
                                      EcoRV

TTAT
```

SODIUM ION BINDING PROTEINS

This invention was made, in part, with government support under grant DCB9018231 from the National Science Foundation. The government may have certain rights in the invention.

TABLE OF CONTENTS

Page
1. FIELD OF THE INVENTION
2. BACKGROUND OF THE INVENTION
3. SUMMARY OF THE INVENTION
4. BRIEF DESCRIPTION OF THE DRAWINGS
5. DETAILED DESCRIPTION OF THE INVENTION
   5.1. THE NhaS CODING SEQUENCE
   5.2. EXPRESSION OF THE NhaS
       5.2.1. EXPRESSION SYSTEMS
       5.2.2. IDENTIFICATION OF TRANSFECTANTS OR TRANSFORMANTS THAT EXPRESS THE NhaS
       5.2.3. RECOVERY OF THE NhaS PROTEIN
   5.3. GENERATION OF ANTIBODIES THAT DEFINE THE NhaS
   5.4. USES OF THE NhaS: SALT TOLERANT PLANTS AND ENGINEERED CELL LINES
6. EXAMPLE: CLONING AND EXPRESSION OF NhaS, A SODIUM ION BINDING PROTEIN
   6.1. MATERIALS AND METHODS
       6.1.1. BACTERIAL STRAINS AND PLASMIDS
       6.1.2. DNA SEQUENCING
       6.1.3. ASSAYS OF $Na^+/H^+$ ANTIPORT AND $Na^+$ BINDING
   6.2. RESULTS

1. FIELD OF THE INVENTION

The present invention relates to the cloning and expression of a sodium ion binding protein. In particular, the invention relates to cloning and expression of a nhaS gene. The nhaS gene product, NhaS, is a protein characterized by binding to and sequestering sodium ion ($Na^+$). The invention further relates to functional fragments of a sodium ion binding protein, which fragments are characterized by their ability to bind to sodium ion. In a specific embodiment, the fragment is a fragment of NhaS. The gene encoding the sodium binding protein can be introduced into cells to produce desalination bioreactors. The gene encoding the sodium binding protein can also be introduced into plants as a transgene to produce plants that are resistant to sodium. The sodium binding protein itself may be used for treatments involving $Na^+/K^+$ ATPase disorders, e.g., in heart disease; the protein also may be introduced parenterally, preferably orally, to bind to and sequester dietary sodium.

2. BACKGROUND OF THE INVENTION $Na^+/H^+$ antiporters are ubiquitous in living cells and have been assigned a large variety of important functions (Boron, W. F., & Boulpaep, E. L. (1983) *J. Gen. Physiol.* 81, 29–52; Krulwich, T. A. (1983) *Biochim. Biophys. Acta* 726, 245–264; Aronson, P. S. (1985) *Annu. Rev. Physiol.* 47, 545–560; Grinstein, S., ed. (1988) $Na^+/H^+$ Exchange CRC Press, Boca Raton, Fla.), the most straight-forward being the regulation of the cytoplasmic level of $Na^+$. The antiporters are integral membrane proteins that carry out either electroneutral or electrogenic exchange of $Na^+$ for $H^+$ that is driven by primary ion translocation events. Several genes encoding eukaryotic (Sardet, C. Franchi, A., & Pouyssegur, J. (1989) *Cell* 56, 271–280; Tse, C. M., Ma, A. I., Yang, V. W., Watson, A. J., Levine, S., Montrose, M. H., Potter, J., Sardet, C., Pouyssegur, J., & Donowitz, M. (1991) *EMBO J.* 10, 1957–1967); Hildebrandt, F., Pizzonia, J. H., Reilly, R. F., Reboucas, N. A., Sardet, C., Pouyssegur, J., Slayman, C. W., Aronson, P. S., & Igarashi, P. (1991) *Biochim. Biophys. Acta* 1129, 105–108; Reilly, R. F., Hildebrandt, R., Biemesderfer, D., Sardet, C., Pouyessegur, J., Aronson, P. S., Slayman, C. W., & Igarashi, P. (1991) *Am. J. Physiol.* 261, F1088–94; Orlowski, J., Kandasamy, R. A., & Shull, G. E. (1992) *J. Biol. Chem.* 267, 9331–9339; Jia, Z. -P., McCullough, N., Martel, R., Hemmingsen, S., & Young, P. G. (1992) *EMBO J.* 11, 1631–1640) and prokaryotic (Goldberg, E. B., Arbel, T. Chen, J. Karpel, R., Mackie, G. A., Schuldiner, S., & Padan, E. (1987) *Proc. Natl. Acad. Sci. U.S.A.* 84, 2615–2619; Karpel, R., Olami, Y., Taglicht, D., Schuldiner, S., & Padan, E. (1988) *J. Biol. Chem.* 263, 10408–10414; Pinner, E., Padan, E., & Schuldiner, S. (1992) *J. Biol. Chem.* 267, 11064–11068; Waser, M., Hess-Bienz, D., Davies, K., & Solioz, M. (1992) *J. Biol. Chem.* 267, 5396–5400) $Na^+/H^+$ antiporters have been cloned, and the gene product of one of these genes, the nhaA gene from *Escherichia coli*, has been purified and studied in proteoliposomes (Taglicht, D., Padan, E., & Schuldiner, S. (1991) *J. Biol. Chem.* 266, 11289–11294). As with other secondary ion porters, no genetic or biochemical evidence has emerged for additional components of these transport systems.

In bacteria, electrogenic $Na^+/H^+$ antiporters may be part of the mechanism for cytoplasmic pH homeostasis in the alkaline range of pH for growth (Krulwich, T. A. (1983) *Biochim. Biophys. Acta* 726, 245–264; Booth, I. R. (1985) *Microbiol. Rev.* 49, 359–378). In particular, electrogenic $Na^+/H^+$ antiport activity appears to be required in order for extremely alkaliphilic bacteria, such as *Bacillus firmus* and *Bacillus alcalophilus*, growing at pH 10.5 to maintain a cytoplasmic pH of 8.3 (Krulwich, T. A., & Guffanti, A. A. (1989) *Annu. Rev. Microbiol.* 43, 435–463). We have taken advantage of $Na^+/H^+$ antiporter-deficient mutants of *Escherichia coli* that have been constructed during the extensive recent dissection of the molecular biology and genetics of the antiport complement in *E. coli* by Padan, Schuldiner and their colleagues (Goldberg, E. B., Arbel, T. Chen, J. Karpel, R., Mackie, G. A., Schuldiner, S., & Padan, E. (1987) *Proc. Natl. Acad. Sci. U.S.A.* 84, 2615–2619; Karpel, R., Olami, Y., Taglicht, D., Schuldiner, S., & Padan, E. (1988) *J. Biol. Chem.* 263, 10408–10414; Pinner, E., Padan, E., & Schuldiner, S. (1992) *J. Biol. Chem.* 267, 11064–11068). Using heterologous complementation of $Na^+/H^+$ antiporter-deficient strains by cloned genes from alkaliphilic *Bacillus firmus* OF4, we have isolated and characterized one putative structural gene for a $Na^+/H^+$ antiporter from the alkaliphile, designated nhaC (Ivey, D. M., Guffanti, A. A., Bossewitch, J. S., Padan, E., & Krulwich, T. A. (1991) *J. Biol. Chem.* 266, 23483–23489). It encodes a membrane protein whose deduced amino acid sequence is consistent with at least ten transmembrane regions and which markedly enhances the $Na^+/H^+$ antiport activity of membranes from *E. coli* NM81; this mutant strain carries a deletion in one of the _E. coli_ antiporter genes (nhaA). Another alkaliphile gene that restored partial Na+ resistance to _E. coli_ NM81 was the product of the alkaliphile cadC gene, a probable cadmium binding protein (Ivey, D. M., Guffanti, A. A., Shen, A., Kudyan, N., & Krulwich, T. A. (1992) _J. Bacteriol._, in press).

3. SUMMARY OF THE INVENTION

The present invention relates to the cloning and expression of a sodium ion binding protein. In particular, the invention is based, in part, on the cloning and expression of a nhaS gene using heterologous complementation of Na+/H+ antiporter-deficient strains by cloned genes from alkaliphilic _Bacillus firmus_ OF4. A clone was isolated and characterized which encoded a putative structural protein for a Na+/H+ antiporter (Ivey, D. M., Guffanti, A. A., Bossewitch, J. S., Padan, E., & Krulwich, T. A. (1991) _J. Biol. Chem._ 266, 23482-23489). Preliminary indications revealed the expression of a small protein product (<10,000 daltons) expressed from the clone carrying the nhaC gene that appeared to fractionate primarily with the membrane (Ivey, D. M., Guffanti, A. A., Bossewitch, J. S., Padan, E., & Krulwich, T. A. (1991) _J. Biol. Chem._ 266, 23483-23489, FIG. 5). Coincident with these observations, further sequence determinations on that clone indicated the presence of a second orf (open reading frame) that could account for the small protein, and whose deduced sequence and location just downstream from an alkaliphile Na+/H+ antiporter gene invited an investigation into its function. The gene product, referred to as NhaS, is a protein characterized by binding to and sequestering sodium ion (Na+).

The invention further relates to functional fragment of a sodium ion binding protein, which fragments are characterized by their ability to bind to sodium ion. In a specific embodiment, the fragment is a fragment of NhaS. The NhaS protein enhances resistance of bacteria into which the nhaS gene has been introduced, to Na+ by sequestering Na+ and reducing its cytotoxicity.

The protein product of the nhaS gene is very basic, with a calculated pI of 12.12. The calculated molecular weight of the full length protein is 7100 Daltons. The NhaS protein has some sequence similarity to genes encoding Na+/K+ ATPases in a region of the N-terminal half of the much larger ATPases. The sequence similarity does not extend to the ATP binding and acylation regions of the ATPases.

In one embodiment, the NhaS protein can be used for modeling drugs that bind to Na+/K+ ATPase, based on the sequence similarity of the proteins. The Na+ binding properties of the NhaS protein make it useful in a variety of medical and agricultural applications, including but not limited to treatments involving Na+/K+ ATPase disorders, e.g., in heart disease; and to bind to and sequester dietary sodium, especially for subjects on a reduced sodium diet or who are suffering from hypertension.

In yet a further embodiment, the nhaS gene can be used to engineer cell lines, in particular plant cell lines, or to prepare transgenic plants. Engineered cell lines containing the nhaS gene, or a Na+ binding fragment thereof, would be useful as desalination bioreactors. Transgenic plants that contain the nhaS gene should be salt resistant.

Thus it is a particular advantage of the present invention that it provides a protein characterized by binding to sodium ion.

It is yet another advantage of the present invention that a gene encoding a protein, which protein is characterized by binding to sodium ion is provided, preferably for introduction into cells or to produce plants transgenic for the gene.

4. BRIEF DESCRIPTION OF THE DRAWINGS

FIG. 3. Transformation of _E. coli_ EP432 by pGRVH enhances sodium resistance. _E. coli_ EP432, transformed with either pGRVH containing nhaS, pBE22 containing the _B. firmus_ OF4 cadC gene (Ivey, D. M., Guffanti, A. A., Shen, A., Kudyan, N., & Krulwich, T. A. (1992) _J. Bacteriol._, in press), or the plasmid control pGEM3Zf(+), were streaked onto LBK plates containing kanamycin and ampicillin, and prepared at the indicated pH values and with the indicated concentrations of NaCl. The photograph was taken after overnight growth at 37° C.

FIG. 5. Hydropathy profile and sequence alignment of the deduced amino acid sequence of the nhaS gene. (A) The Kyte-Doolittle (Kyte, J., & Doolittle, R. F. (1982) _J. Mol. Biol._ 157, 105-132) profile was generated using a window of 9 amino acid residues, and the profile using the algorithm of Engelman et al. (Engelman, D. M., Steitz, T. A., & Goldman, A. (1986) _Annu. Rev. Biophys. Biophys. Chem._ 15, 321-353) was generated using a window of 20 amino acids residues. (B) Alignment of NhaS with a region of the α chain of the Na+/K+ ATPase of _Drosophila melanogaster_ (Lebovitz, R. M., Takeyasu, K., & Fambrough, D. M. (1989) _EMBO J._ 8, 193-202). Identities are denoted by the vertical dashes and conservative replacements are denoted by the dots.

5. DETAILED DESCRIPTION OF THE INVENTION

The gene identified in this study is immediately downstream from a putative structural gene for an alkaliphile Na+/H+ antiporter, nhaC, and is likely to be transcribed together with nhaC. The gene product is apparently a small Na+ binding protein that functions on the cytoplasmic side of the membrane, as opposed to the classic larger periplasmic binding proteins that have been extensively characterized in prokaryotes (Quiocho, F. A. (1990) *Phil. Trans. R. Soc. Lond.* B 326, 341–351). The Na+ binding assay indicates that crude extracts containing levels of cloned gene product that are insufficient to identify the protein on Coomassie blue-stained gels in comparisons with control extracts, result in binding activity up to 10-fold that of those in control extracts. The sequestration of Na+ probably plays a major role in restoring Na+-resistance to antiporter-deficient mutants of *E. coli*. We thus propose to call the gene encoding the Na+ binding protein nhaS.

The present invention relates to the cloning and expression of nhaS. In particular, the invention relates to cloning and expression of a nhaS gene. The nhaS gene product, NhaS, is a protein characterized by binding to and sequestering sodium ion (Na+). The invention further relates to functional fragment of a sodium ion binding protein, which fragments are characterized by their ability to bind to sodium ion. In a specific embodiment, the fragment is a fragment of NhaS.

The NhaS protein is associated especially with alkaliphilic bacteria, which are highly dependent on Na+ regulation for pH homeostasis. In particular, these bacteria need to maintain a cytoplasmic pH that is much more acidic than the external medium when the latter is well above pH 10. The NhaS protein enhances resistance of bacteria or other cells into which the nhaS gene has been introduced to Na+ by sequestering Na+ and reducing its cytotoxicity. In bacteria, the protein appears to operate on the cytoplasmic side of the membrane.

The protein product of the nhaS gene is very basic, with a calculated pI of 12.12. The calculated molecular weight of the full length protein is 7100 Daltons. The NhaS protein has some sequence similarity to genes encoding Na+/K+ ATPases in a region of the N-terminal half of the much larger ATPases. The sequence similarity does not extend to the ATP binding and acylation regions of the ATPases.

In one embodiment, the NhaS protein can be used for modeling drugs that bind to Na+/K+ ATPase, based on the sequence similarity of the proteins.

The Na+ binding properties of the NhaS protein make it useful in a variety of medical and agricultural applications. For example, the protein may be useful for treatments involving Na+/K+ ATPase disorders, e.g., in heart disease. In another embodiment, the NhaS protein can be introduced parenterally, preferably orally, to bind to and sequester dietary sodium, especially for subjects on a reduced sodium diet or who are suffering from hypertension. In a further embodiment, the protein is immobilized on a solid support such as a membrane or resin which can be used to remove Na+ from chemicals or during dialysis.

In yet a further embodiment, the nhaS gene can be used to engineer cell lines, in particular plant cell lines, or to prepare transgenic plants. Engineered cell lines containing the nhaS gene, or a Na+ binding fragment thereof, would be useful as desalination bioreactors. Transgenic plants that contain the nhaS gene should be salt resistant. Such plants may resist drought conditions, or be suitable for cultivation in briny soil or salt marshes.

For clarity of discussion, the invention is described in the subsections below by way of example for the *Bacillus firmus* sodium ion binding protein NhaS. However, the principles may be analogously applied to clone and express the NhaS or sodium ion binding proteins of other species, especially alkaliphilic bacteria.

5.1. THE NhaS CODING SEQUENCE

The invention relates to isolated nucleic acids encoding a sodium ion binding protein. The invention further relates to a cell line stably containing a recombinant nucleic acid encoding a sodium ion binding protein. In another embodiment, the invention relates to a nucleic acid encoding a fragment of the sodium ion binding protein, which fragment binds sodium ion.

Figure 1:
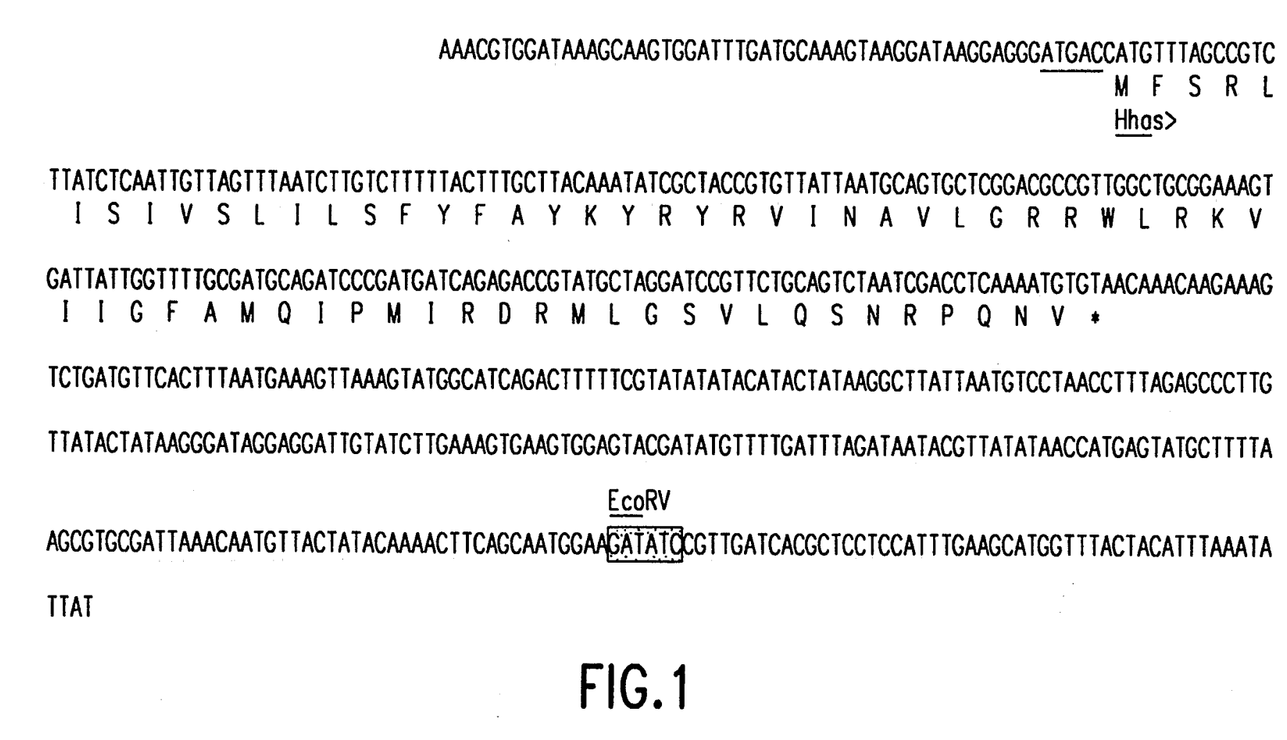
FIG. 1. Nucleotide and deduced amino acid sequence of the nhaS gene and surrounding region. The insert of pGRVH is comprised of the sequence from the HindIII site to the EcoRV site.
Figure 5A:
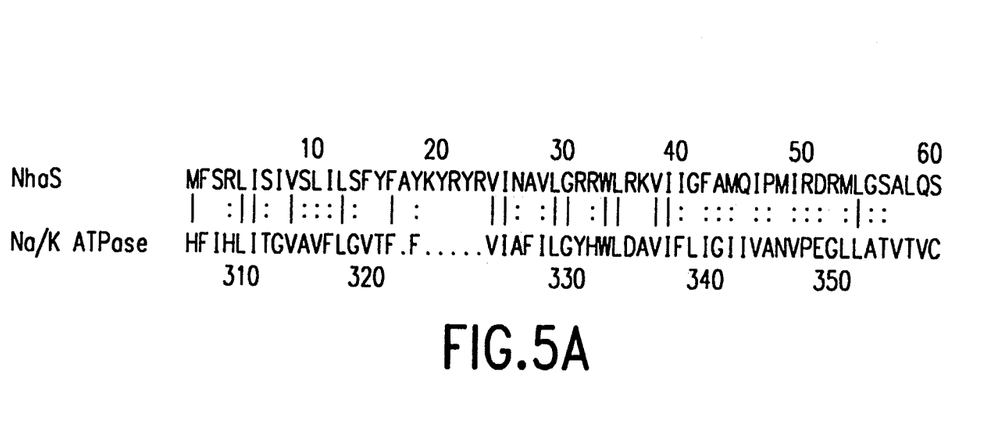
Figure 5B:
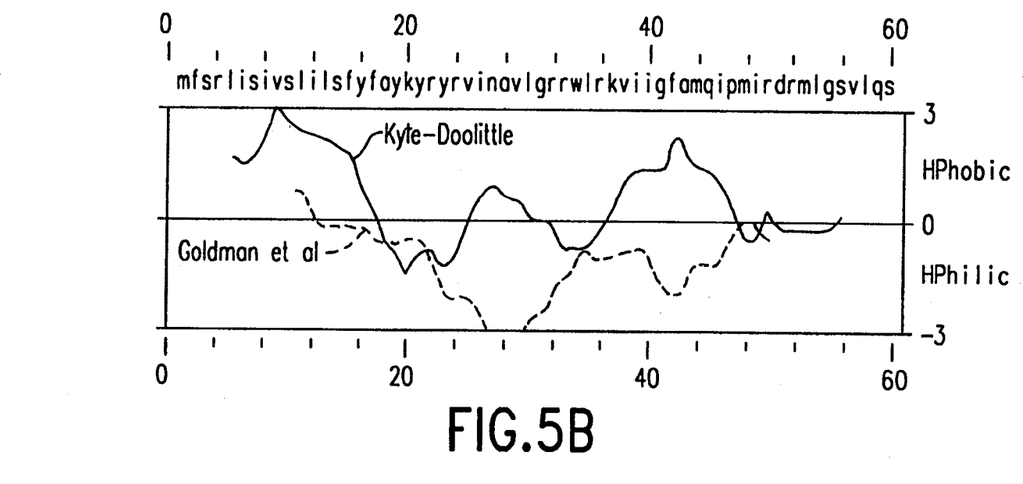

The nucleotide coding sequence (SEQ. ID NO: 1) and deduced amino acid sequence (SEQ. ID NO: 2) for the *Bacillus firmus* OF4 nhaS gene are depicted in FIG. 1. The open reading frame encodes a 67 amino acid protein of about 7100 Daltons. Hydrophobicity analysis of the deduced protein (FIG. 5) suggests the possibility that the gene product, NhaS, associates with the membrane. This is consistent with the retention of NhaS protein in everted membrane vesicle preparations, evidence of membrane binding ability.

This unusual protein is further characterized by its extraordinary basicity. The overall predicted pI of NhaS is 12.1. This basicity may facilitate association with negatively charged phospholipids in the membrane, and it may also function as a pH sensor, rendering Na+ binding sensitive to pH.

The NhaS protein is further characterized by sequence similarity to numerous cloned genes encoding the α chain of the Na+/K+ ATPase from various species and tissues, e.g., from *Drosophila melanogaster*. This region of the Na+/K+ ATPase has been proposed to encompass parts of two putative membrane-spanning stretches in the N-terminal half of the molecule, and the small intervening loop that contains the tryptophan shown in common with NhaS. The loop also shows similarity with a small region of sequence in the gene encoding the cardiac sarcolemmal Na+/Ca++ exchanger. However, the NhaS protein is further characterized by having a dramatically basic deduced sequence—KYRYK—that has no analog in the ATPase sequences (and thus requires introduction of a gap in the ATPase sequences in order to maximize similarity). Such a region in the NhaS protein clearly contributes to overall basicity, and likely has a role in the pH-dependence of the Na+-binding activity.

The invention also relates to nhaS genes isolated from other bacterial species especially from alkaliphilic species, including but not limited to Bacillus, such as *B. alcalophilus*, *B. firmus*, and *Exiguobacterium aurantiacum*, in which is believed NhaS activity exists. Members of the NhaS family are defined herein as those small proteins that bind Na+. Such Na+ binding proteins may demonstrate about 80% homology at the nucleotide level, and even 90% homology at the amino acid level. The alkaliphilic *B. firmus* sequence can be used to design degenerate or fully degenerate oligonucleotide probes which can be used to screen genomic libraries derived from appropriate bacterial which express NhaS. The N-terminus of the sequence depicted in FIG. 1 may advantageously be used to design such oligonucleotide probes, as this region is relatively conserved with Na+/K+ ATPases, and thus should be conserved within the NhaS family.

Alternatively, a polymerase chain reaction (PCR) based strategy may be used to clone nhaS. Two pools of degenerate oligonucleotides, corresponding to conserved motifs between the NhaS and Na+/K+ ATPases may be designed to serve as primers in a PCR reaction. Examples of such conserved motifs which may be used include but are not limited to those found at the N-terminus. The template for the reaction is chromosomal DNA prepared from a bacterial strain known or expected to express NhaS. The amplified PCR fragment may be used to isolate a full length nhaS clone by radioactively labeling the amplified fragment and screening a library.

Alternatively, the methods detailed in Section 6.1.1 infra, for cloning the nhaS DNA, may be utilized to obtain the corresponding nhaS DNA sequence from other bacterial species. Specifically, a genomic library constructed from DNA prepared from a bacterial strain known or expected to express a Na+ binding protein may be used to transform the bacterial strain NM81 which is deficient in the putative Na+/H+ antiporter. Transformation of a recombinant plasmid coding for a sodium binding protein into an antiporter-deficient NM81 bacterial strain would be expected to enhance the Na+-resistance of the bacteria, and this phenotype may be selected for by adjusting the Na+ content and pH of the medium.

Cloning of other proteins in the nhaS family may be carried out in a number of different ways. The PCR based strategy described above for cloning of nhaS, may also be used to isolate encoding NhaS related proteins. Alternatively, a bacteriophage library may be screened, under conditions of reduced stringency, using a radioactively labeled fragment of the B. firmus nhaS clone. For a review of cloning strategies which may be used, see e.g., Maniatis, 1989, Molecular Cloning, A Laboratory Manual, Cold Springs Harbor Press, New York; and Ausubel et al., 1989, Current Protocols in Molecular Biology, Green Publishing Associates and Wiley Interscience, New York.

In accordance with the invention, nucleotide sequences which encode a NhaS, fragments, fusion proteins or functional equivalents thereof, may be used to generate recombinant DNA molecules that direct the expression of the NhaS, or a functionally active peptide, fusion protein or functional equivalent thereof, in appropriate host cells. Alternatively, nucleotide sequences which hybridize to portions of the nhaS sequence may also be used in nucleic acid hybridization assays, Southern and Northern blot analyses, etc.

Due to the degeneracy of the genetic code, other DNA sequences which encode substantially the NhaS amino acid sequence, e.g., such as the deduced sequence depicted in FIG. 1, or a functional equivalent may be used in the practice of the present invention for the cloning and expression of the nhaS. Such DNA sequences include those which are capable of hybridizing to the nhaS sequence under stringent conditions, or which would be capable of hybridizing under stringent conditions but for the degeneracy of the genetic code. The stringency conditions may be adjusted in a number of ways. For example, when performing polymerase chain reactions (PCR), the temperature at which annealing of primers to template takes place or the concentration of $MgCl_2$ in the reaction buffer may be adjusted. When using radioactively labeled DNA fragments or oligonucleotides to probe filters, the stringency may be adjusted by changes in the ionic strength of the wash solutions or by careful control of the temperature at which the filter washes are carried out.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the NhaS sequence, which result in a silent change thus producing a functionally equivalent NhaS. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, theonine; phenylalanine, tyrosine. As used herein, a functionally equivalent NhaS refers to a protein which binds sodium ion (Na+), but not necessarily with the same binding affinity of its counterpart native NhaS.

The DNA sequences of the invention may be engineered in order to alter the NhaS coding sequence for a variety of ends including but not limited to alterations which modify expression of the gene product. For example, mutations may be introduced using techniques which are well known in the art, e.g. site-directed mutagenesis, to insert new restriction sites that facilitate cloning into expression vectors. In an embodiment of the invention, the nhaS or a modified nhaS sequence may be ligated to a heterologous sequence to encode a fusion protein. The fusion protein may be engineered to contain a cleavage site located between the NhaS sequence and the heterologous protein sequence, so that the NhaS can be cleaved away from the heterologous moiety.

In an alternate embodiment of the invention, the coding sequence of nhaS could be synthesized in whole or in part, using chemical methods well known in the art. See, for example, Caruthers, et al., 1980, Nuc. Acids Res. Symp. Ser. 7: 215–233; Crea and Horn, 180, Nuc. Acids Res. 9(10): 2331; Matteucci and Caruthers, 1980, Tetrahedron Letters 21: 719; and Chow and Kempe, 1981, Nuc. Acids Res. 9(12): 2807–2817. Alternatively, the protein itself could be produced using chemical methods to synthesize the NhaS amino acid sequence in whole or in part. For example, peptides can be synthesized by solid phase techniques, cleaved from the resin, and purified by preparative high performance liquid chromatography. (E.g., see Creighton, 1983, Proteins Structures And Molecular Principles, W. H. Freeman and Co., New York pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., New York, pp. 34–49.

5.2. EXPRESSION OF THE NhaS

In order to express a biologically active NhaS, the nucleotide sequence coding for NhaS, or a functional equivalent as described in Section 5.1 supra, is inserted into an appropriate expression vector, i.e., a vector which contains the necessary elements for the transcription and translation of the inserted coding sequence. The nhaS gene products as well as host cells or cell lines transfected or transformed with recombinant nhaS expression vectors can be used for a variety of purposes. These include but are not limited to generating antibodies (i.e., monoclonal or polyclonal) that bind to the receptor, including those that competitively inhibit Na+ binding and "neutralize" NhaS activity.

5.2.1. EXPRESSION SYSTEMS

Methods which are well known to those skilled in the art can be used to construct expression vectors containing the nhaS coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, New York and Ausubel et al., 1989, Current Protocols in Molecular Biology, Greene Publishing Associates and Wiley Interscience, New York.

A variety of host-expression vector systems may be utilized to express the nhaS coding sequence. These include but are not limited to microorganisms such as bacteria transformed with recombinant bacteriophage DNA, plasmid DNA or cosmid DNA expression vectors containing the nhaS coding sequence; yeast transformed with recombinant yeast expression vectors containing the nhaS coding sequence; insect cell systems infected with recombinant virus expression vectors (e.g., baculovirus) containing the nhaS coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the nhaS coding sequence; or animal cell systems infected with recombinant virus expression vectors (e.g., adenovirus, vaccinia virus) including cell lines engineered to contain multiple copies of the nhaS DNA either stably amplified (e.g., CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the nhaS DNA SV40-, BPV- and EBV-based vectors may be used with an appropriate selectable marker.

In bacterial systems a number of expression vectors may be advantageously selected depending upon the use intended for the NhaS expressed. For example, when large quantities of NhaS are to be produced for structural studies and protein modelling or for use in an immobilized form to sequester Na+ vectors which direct the expression of high levels of fusion protein products that are readily purified may be desirable. Such vectors include but are not limited to the *E. coli* expression vector pUR278 (Ruther et al., 1983, EMBO J. 2: 1791), in which the nhaS coding sequence may be ligated into the vector in frame with the lac Z coding region so that a hybrid NhaS-lac Z protein is produced; pIN vectors (Inouye & Inouye, 1985, Nucleic acids Res. 13: 3101–3109; Van Heeke & Schuster, 1989, J. Biol. Chem. 264: 5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned NhaS polypeptide can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, New York, Vol. 153, pp. 516–544; Glover, 1986, DNA Cloning, Vol. II, IRL Press, Washington, D.C., Ch. 3; and Bitter, 1987, Heterologous Gene Expression in Yeast, Methods in Enzymology, Eds. Berger & Kimmel, Acad. Press, New York, Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the nhaS coding sequence may be driven by any of a number of promoters. For example, viral promoters such as the 35S RNA and 19S RNA promoters of CaMV (Brisson et al., 1984, Nature 310: 511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224: 838–843); or heat shock promoters, e.g., soybean hsp17.5-E or hsp17.3-B (Gurley et al., 1986, Mol. Cell. Biol. 6: 559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, New York, Section VIII, pp. 421–463; and Grierson & Corey, 1988, Plant Molecular Biology, 2d Ed., Blackie, London, Ch. 7–9.

An alternative expression system which could be used to express NhaS is an insect system. In one such system, *Autographa californica* nuclear polyhedrosis virus (AcNPV) is used as a vector to express foreign genes. The virus grows in *Spodoptera frugiperda* cells. The nhaS coding sequence may be cloned into non-essential regions (for example the polyhedrin gene) of the virus and placed under control of an AcNPV promoter (for example the polyhedrin promoter). Successful insertion of the nhaS coding sequence will result in inactivation of the polyhedrin gene and production of non-occluded recombinant virus (.i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46: 584; Smith, U.S. Pat. No. 4,215,051).

In mammalian host cells, a number of viral based expression systems may be utilized. In cases where an adenovirus is used as an expression vector, the nhaS coding sequence may be ligated to an adenovirus transcription/translation control complex, e.g., the late promoter and tripartite leader sequence. This chimeric gene may then be inserted in the adenovirus genome by in vitro or in vivo recombination. Insertion in a nonessential region of the viral genome (e.g., region E1 or E3) will result in a recombinant virus that is viable and capable of expressing NhaS in infected hosts. (E.g., See Logan & Shenk, 1984, Proc. Natl. Acad. Sci. (USA) 81: 3655-3659). Alternatively, the vaccinia 7.5K promoter may be used. (E.g., see Mackett et al., 1982, Proc. Natl. Acad. Sci. (USA) 79: 7415-7419; Mackett et al., 1984, J. Virol. 49: 857-864; Panicali et al., 1982, Proc. Natl. Acad. Sci. 79: 4927-4931).

Specific initiation signals may also be required for efficient translation of inserted nhaS coding sequences. These signals include the ATG initiation codon and adjacent sequences, referred to as Kosak sequences, which differ from those utilized by prokaryotes. In cases where only a portion of the nhaS coding sequence is inserted, exogenous translational control signals, including the ATG initiation codon, must be provided. Furthermore, the initiation codon must be in phase with the reading frame of the nhaS coding sequence to ensure translation of the entire insert. These exogenous translational control signals and initiation codons can be of a variety of origins, both natural and synthetic. In addition, eukaryotic expression vectors should contain the signals necessary for transcriptional termination and polyadenylation. The efficiency of expression may be enhanced by the inclusion of appropriate transcription enhancer elements, transcription terminators, etc. (see Bitter et al., 1987, Methods in Enzymol. 153: 516-544).

For long-term, high-yield production of recombinant proteins, stable expression is preferred. For example, cell lines which stably express the NhaS may be engineered. Rather than using expression vectors which contain viral origins of replication, host cells can be transformed with the nhaS DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NhaS on the cytoplasmic surface of the cell membrane, and which bind $Na^+$.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk, hgprt or aprt cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.2.2. IDENTIFICATION OF TRANSFECTANTS OR TRANSFORMANTS THAT EXPRESS THE NhaS

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of nhaS mRNA transcripts in the host cell; and (d) detection of the gene product as measured by immunoassay or by its biological activity.

In the first approach, the presence of the nhaS coding sequence inserted in the expression vector can be detected by DNA-DNA or DNA-RNA hybridization using probes comprising nucleotide sequences that are homologous to the nhaS coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the nhaS coding sequence is inserted within a marker gene sequence of the vector, recombinants containing the nhaS coding sequence can be identified by the absence of the marker gene function. Alternatively, a marker gene can be placed in tandem with the nhaS sequence under the control of the same or different promoter used to control the expression of the nhaS coding sequence. Expression of the marker in response to induction or selection indicates expression of the nhaS coding sequence.

In the third approach, transcriptional activity for the nhaS coding region can be assessed by hybridization assays. For example, RNA can be isolated and analyzed by Northern blot using a probe homologous to the nhaS coding sequence or particular portions thereof. Alternatively, total nucleic acids of the host cell may be extracted and assayed for hybridization to such probes.

In the fourth approach, the expression of the NhaS protein product can be assessed immunologically, for example by Western blots, immunoassays such as radioimmuno-precipitation, enzyme-linked immunoassays and the like. The ultimate test of the success of the expression system, however, involves the detection of the biologically active NhaS gene product. A number of assays can be used to detect receptor activity including but not limited to $Na^+$ binding assays.

5.2.3. RECOVERY OF THE NhaS PROTEIN

Once a clone that produces high levels of biologically active NhaS is identified, the clone may be expanded and used to produce large amounts of the protein, which may be purified using techniques well-known in the art including, but not limited to immunoaffinity purification, chromatographic methods including high performance liquid chromatography or more preferably cation exchange chromatography, "affinity" chromatography based on the affinity of NhaS for $Na^+$, immunoaffinity purification using antibodies and the like.

Where the nhaS coding sequence is engineered to encode a cleavable fusion protein, purification may be readily accomplished using affinity purification techniques. For example, a collagenase cleavage recognition consensus sequence may be engineered between the carboxy terminus of NhaS and protein A. The resulting fusion protein may be readily purified using an IgG column that binds the protein A moiety. Unfused NhaS may be readily released from the column by treatment with collagenase. Another example would be the use of pGEX vectors that express foreign polypeptides as fusion proteins with glutathionine S-transferase (GST). The fusion protein may be engineered with either thrombin or factor Xa cleavage sites between the cloned gene and the GST moiety. The fusion protein may be easily purified from cell extracts by adsorption to glutathione agarose beads followed by elution in the presence of glutathione. In this aspect of the invention, any cleavage site or enzyme cleavage substrate may be engineered between the NhaS sequence and a second peptide or protein that has a binding partner which could be used for purification, e.g., any antigen for which an immunoaffinity column can be prepared.

5.3. GENERATION OF ANTIBODIES THAT DEFINE THE NhaS PROTEIN

Various procedures known in the art may be used for the production of antibodies to epitopes of the recombinantly produced NhaS. Neutralizing antibodies i.e., those which compete for the $Na^+$ binding site of the receptor are especially preferred for diagnostics and therapeutics. Such antibodies include but are not limited to polyclonal, monoclonal, chimeric, single chain, Fab fragments and fragments produced by an Fab expression library.

For the production of antibodies, various host animals may be immunized by injection with the NhaS including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and corynebacterium parvum.

Monoclonal antibodies to NhaS may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce NhaS-specific single chain antibodies.

Antibody fragments which contain specific binding sites of NhaS may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity to NhaS.

5.4. USES OF THE NhaS: SALT TOLERANT PLANTS AND ENGINEERED CELL LINES

The nhaS DNA, NhaS expression products, antibodies and engineered cell lines described above have a number of uses as a dietary therapy where control of sodium intake is desired, or for preparing recombinant plants capable of growth in briney water or under drought conditions.

In another embodiment of the invention, the NhaS itself, or a fragment containing its $Na^+$ binding site, could be administered in vivo. Preferably a NhaS fragment lacks the membrane-binding portion of the protein. The free NhaS or the soluble peptide fragment could bind $Na^+$, thus reducing side effects in vivo.

Recently, computer generated models for interactions have been developed and in a specific embodiment of the invention information derived from computer modeling of NhaS may be used for design of inhibitors of the $Na^+/K^+$ ATPase. Changes made to NhaS sequences, using for example techniques for site directed mutagenesis and expression of mutant proteins in cell lines, may be used to further define the functional role of particular protein regions and residues.

Nucleic acids, in particular vectors, are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

6. EXAMPLE: CLONING AND EXPRESSION OF NhaS, A SODIUM ION BINDING PROTEIN

A gene, designated nhaS, has been identified downstream from the putative Na+/H+ antiporter-encoding nhaC gene on the chromosome of alkaliphilic *Bacillus firmus* OF4. The deduced nhaS gene product would be a protein with an Mr of 7,000, a pI of 12.12, and shared sequence similarity to a region in the N-terminal half of the Na+/K+ ATPase. An *Escherichia coli* strain with a deletion in one Na+/H+ antiporter gene (nhaA) exhibited enhanced activity of its residual, nhaB-dependent membrane antiport activity when transformed with a plasmid containing nhaS. An *E. coli* mutant that was deleted in both nhaA and nhaB showed no significant increase in Na+/H+ antiport when transformed with the same plasmid, but nonetheless showed greatly enhanced resistance to high concentrations of NaCl relative to a control transformant. Direct evidence for a Na+-binding activity of the nhaS product in extracts of the *E. coli* transformant was obtained using a sodium sensitive fluorescent probe. NhaS is proposed to be a sodium binding protein that can enhance the Na+-resistance of antiporter-deficient strains by increasing the availability of Na+ to the integral membrane antiporters on the cytoplasmic side of the membrane and by sequestering Na+ while rate-limiting efflux mechanisms catalyze extrusion of the cation.

6.1. MATERIALS AND METHODS

6.1.1. BACTERIAL STRAINS AND PLASMIDS

The cloned DNA fragment from alkaliphilic *B. firmus* OF4 that was the starting point for this investigation was in pGJX5 is a derivative of pM4.10, which had been selected from a library of MboI-digested *B. firmus* OF4 DNA. Chromosomal DNA was prepared from *B. firmus* OF4 by the method of Marmur (1961, J. Mol. Biol. 3:208–218). The chromosomal DNA was partially digested with MboI (at 0.04 unit/μg chromosomal DNA) and ligated into BamHI-digested and dephosphorylated pSPT18 ("library 1") or pGEM3Zf(+) ("library 2"). Recombinant plasmids were transformed into *E. coli* JM109, and approximately 105 colonies were pooled, inoculated into 50 ml of LB containing ampicillin, and grown overnight at 37° C. Plasmid DNA was isolated (Del Sal et al., 1989, BioTechniques 7:514–519) and used for transformation of NM81. Analyses of the subsequent clones were conducted in part by Southern analysis and by other standard restriction mapping and subcloning techniques (Ausubel et al. (eds.), 1987, *Current Protocols in Molecular Biology*, John Wiley & Sons, New York; Sambrook et al., 1989, Molecular Cloning: A Laboratory Manual, 2nd Ed., Cold Spring Harbor Laboratory, Cold Spring Harbor, N.Y.). Probe DNA used for Southern analyses was radioactively labeled using the Prime-a-Gene kit (Promega). Subcloning study was carried out by standard molecular biological manipulations (Ausubel et al. (eds.), 1987, *Current Protocols in Molecular Biology*, John Wiley & Sons, New York). *E. coli* strain NM81 ($\Delta$nhaA, kan$^R$) (Padan, E., Maisler, N., Taglicht, D., Karpel, R., & Schuldiner, S. (1989) *J. Biol. Chem.* 264, 20297–20302) and *E. coli* strain EP432 ($\Delta$nhaA, $\Delta$nhaB, kan$^R$, cam$^R$) (EP432) were obtained from Dr. Etana Padan (Institute for Life Sciences, Hebrew University, Jerusalem, Israel). These strains were routinely grown on LBK medium (Goldberg, E. B., Arbel, T., Chen, J., Karpel, R., Mackie, G. A., Schuldiner, S., & Padan, E. (1987) *Proc. Natl. Acad. Sci. U.S.A.* 84, 2615–1619) at pH 7.5, containing 50 μg/ml kanamycin and, when transformed with plasmids, 100 μg/ml ampicillin. For specific determinations of Na+ resistance, the Na+ content and pH of the medium were adjusted as indicated.

6.1.2. DNA SEQUENCING

CsCl gradient-purified plasmid DNA was prepared by a large scale alkaline lysis procedure for DNA sequencing (Ausubel, F. M., Brent, R., Kingston, R. E., Moore, D. D., Smith, J. A., Seidman, J. G., & Struhl, K. (eds.) (1987) *Current Protocols in Molecular Biology*, John Wiley & Sons, Inc., New York). Both strands of the regions of interest were sequenced using an Applied Biosystems 373A DNA sequencer in the DNA Core Laboratory of the Brookdale Center for Molecular Biology at the Mount Sinai School of Medicine. Oligonucleotide primers were synthesized in the same facility using the Applied Biosystems 380B DNA synthesizer. The Genetics Computer Group Sequence Analysis Software Package (Devereux, J., Haeberli, P., & Smithies, O. (1984) *Nucl. Acids Res.* 12, 387–395) was used for sequence analyses on a VAX 4000-300 computer.

6.1.3. ASSAYS OF Na+/H+ ANTIPORT AND Na+ BINDING

Assays of antiport were carried out on everted membrane preparations from transformed *E. coli* strains. The vesicles were prepared according to the method of Rosen and colleagues (Ambudkar, S. V., Zlotnick, G. W., & Rosen, B. P. (1984) *J. Biol. Chem.* 259, 6142–6146; Rosen, B. P. (1986) *Methods Enzymol.* 125, 328–336), with a few modifications as described by Goldberg et al. (Goldberg, E. B., Arbel, T., Chen, J., Karpel, R., Mackie, G. A., Schuldiner, S., & Padan, E. (1987) *Proc. Natl. Acad. Sci. U.S.A.* 84, 2615–1619) and Ivey et al. (Ivey, D. M., Guffanti, A. A., Bossewitch, J. S., Padan, E., & Krulwich, T. A. (1991) *J. Biol. Chem.* 266, 23483–23489). Several accommodations were made to the apparent lability of the alkaliphile gene product(s) in this heterologous system. Specifically, cells were grown from small inocula for about 8 h, harvested, and immediately used for membrane preparations, without freezing or storage in the cold. The membranes were assayed immediately after preparation. Protein concentrations were determined by the method of Lowry (1951, J. Biol. Chem., 193:256–275) using egg white lysozyme as a standard. The membranes were assayed immediately after preparation. For assays of Na+ binding, crude extracts were prepared by passing cells through a French Press (10,000 lb/in2). Unbroken cells and cell wall debris were separated by centrifugation at 12,000×g for ten minutes. The supernatant was then dialyzed (in tubing) with a molecular weight cut-off of 3,500 daltons) for five hours against 20 mM Tris-Hepes, pH 7.5, with two changes of buffer. Protein was determined by the method of Lowry (Lowry, O. H., Rosebrough, N. J., Farr, A. L., & Randall, R. J. (1951) *J. Biol. Chem.* 193,265–275) using egg white lysozyme as the standard.

The antiport assays of everted vesicles involved the establishment of a $\Delta$pH (transmembrane pH gradient) by the addition of D-lactate to the membrane suspension, followed by the partial abolition of that gradient by the addition of NaCl or LiCl. The establishment and abolition of the Δ was monitored by the quenching of acridine orange fluorescence and its reversal (Goldberg, E. B., Arbel, T., Chen, J., Karpel, R., Mackie, G. A., Schuldiner, S., & Padan, E. (1987) *Proc. Natl. Acad. Sci. U.S.A.* 84, 2615-1619; Ambudkar, S. V., Zlotnick, G. W., & Rosen, B. P. (1984) *J. Biol. Chem.* 259, 6142-6146). A Perkin-Elmer Cetus model 650-10S spectrofluorometer was used, with an excitation wavelength of 430 nm and emission wavelength of 570 nm.

The $Na^+$ binding assay was conducted on cell extracts using SBFI (Harootunian, A. R., Kao, J. P. Y., Eckert, B. K., & Tsien, R. Y. (1989) *J. Biol. Chem.* 264, 19458-19467). Crude extract was preincubated for five minutes in 20 mM Tris-Hepes, pH 7.5, with 5 μM SBFI in the presence of various concentrations of NaCl. Fluorescence was monitored at a fixed emission wavelength of 505 nm, while the excitation wavelength was scanned between 300 and 400 nm.

6.2. RESULTS

Further sequence analysis of the cloned alkaliphile DNA fragment in pGJX5, downstream from nhaC, indicated the presence of an open reading frame (orf2) starting 50 bp downstream from nhaC. The next closest downstream open reading frame was an additional 400 bp beyond orf2. The nucleotide sequence and the deduced amino acid sequence of a product that orf2 might encode are shown in FIG. 1. The putative product would be a very basic protein, with a pI of 12.12 and a molecular weight of 7,100 daltons. The databases indicated that this gene was novel and that it had some sequence similarity to genes encoding $Na^+/K^+$ ATPases in a region of the N-terminal half of these much larger proteins, distinct from the ATP binding and acylation regions. Given this similarity and the proximity to nhaC on the alkaliphile chromosome, we sought to examine the activity of the orf2 gene product in *E. coli* strains with deletions in one or both of the $Na^+/H^+$ antiporter-encoding genes.

Figure 2A:
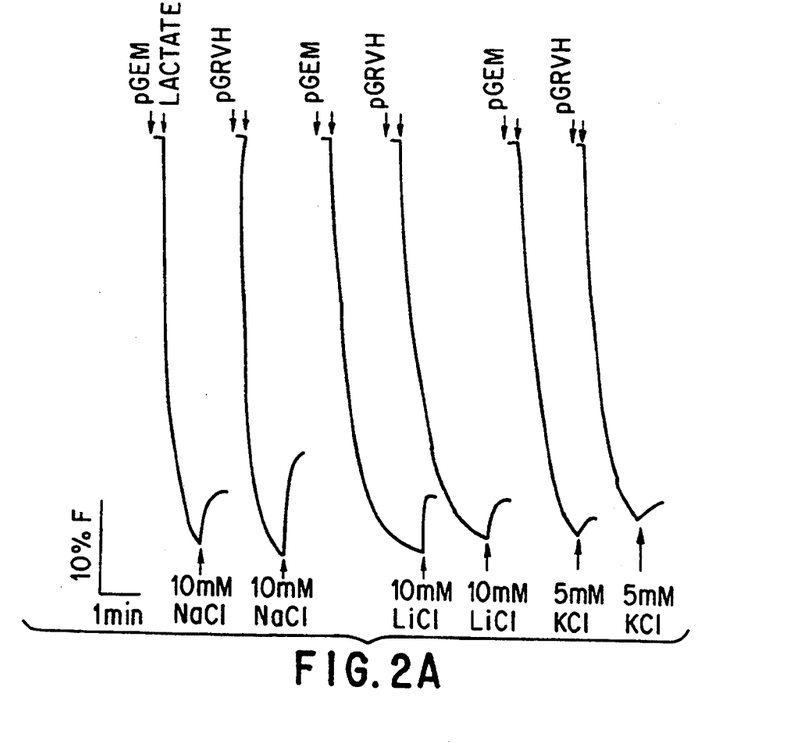
FIG. 2. Antiport activity of everted membrane vesicles prepared from _E. coli_ NM81 and EP432 transformed with either the nhaS-containing pGRVH or control plasmid pGEM3Zf(+). Quenching of acridine orange fluorescence was initiated by addition of D-lactate (as indicated by the right most arrow at the top of each tracing). Antiport activity is taken as the reversal of quenching upon addition of the salt (bottom arrows). Transformed NM81 (A) was assayed for Na+, Li+, K+ or antiport with protons at pH 8.0. Transformed EP432 (B) was assayed for Na+/H+ antiport, either with or without prior addition of KCl, as indicated by the arrows.
Figure 2B:
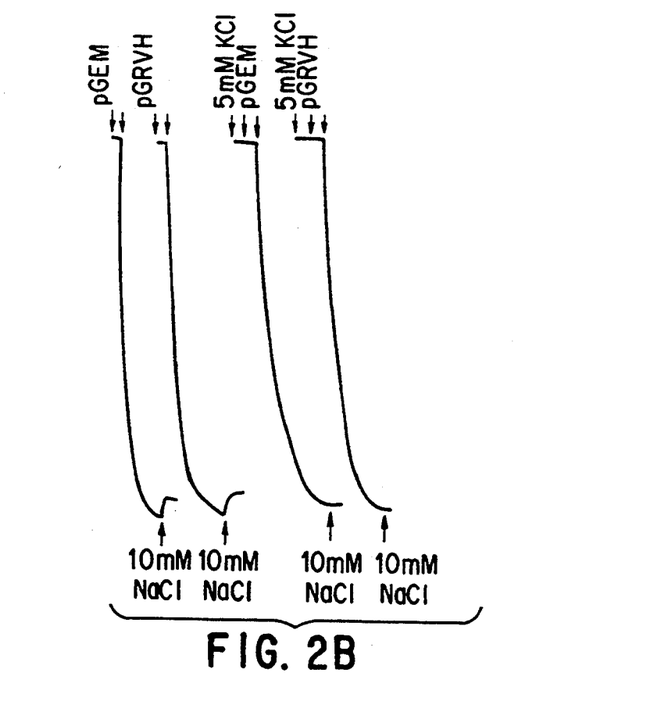
Figure 3A:
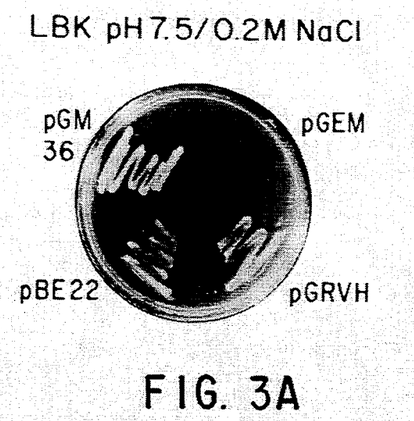
Figure 3B:
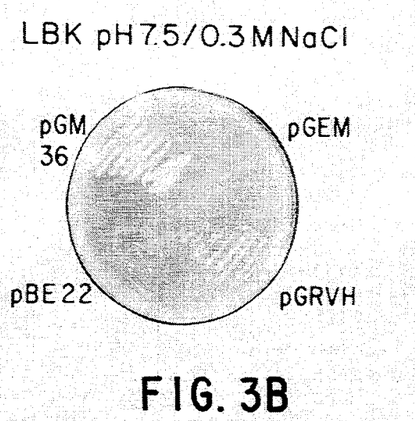
Figure 3C:
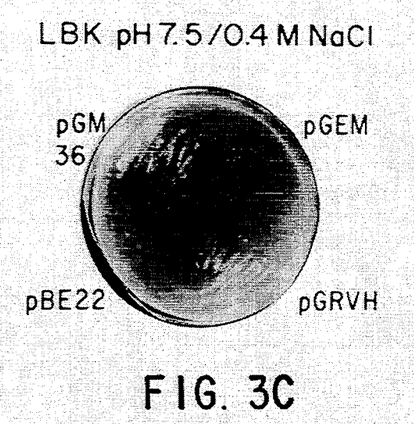
Figure 3D:
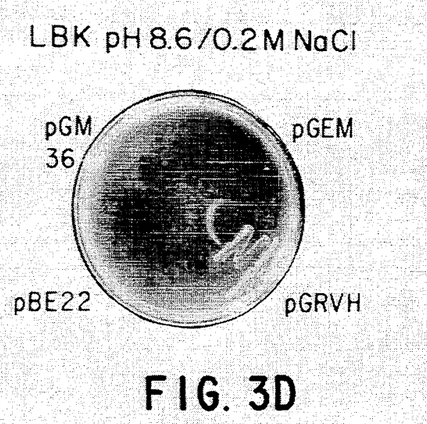

A subclone (pGRVH) in pGEM7f(+) containing orf2 as the sole complete open reading frame was constructed from pGJX5 by digesting this plasmid with HindIII, which cut 77 bp upstream from the 3' end of nhaC, and with EcoRV, which cut 270 bp downstream from orf2, well before the start of the next downstream open reading frame (FIG. 1). As shown in FIG. 2, a pGRVH transformant of the nhaA-deletion strain, *E. coli* NM81, exhibited enhanced membrane $Na^+/H^+$ antiport activity with $Na^+$ but not with $Li^+$ as the substrate, relative to a control transformed with plasmid alone. By contrast, a pGRVH transformant of *E. coli* strain EP432, that carries deletions in both the nhaA and nhaB genes, did not show such enhancement. *E. coli* EP432 exhibited only a slight $Na^+/H^+$ antiport activity that was not significantly enhanced in the membranes of the pGRVH transformant. In the presence of excess KCl, the $Na^+/H^+$ antiport was no longer observed, consistent with the conclusion that this small residual activity is attributable to a $K^+/H^+$ antiporter in the membrane (EP432). Under these conditions, the presence of pGRVH had no effect on the antiport activity (FIG. 2).

Figure 4A:
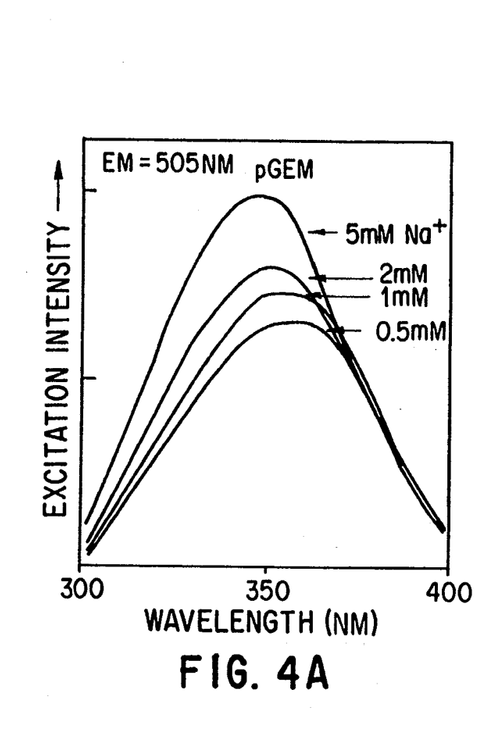
FIG. 4. The effect of sodium ion concentration upon the excitation intensity of SBFI in the absence or presence of extracts in which the nhaS gene is expressed. A) Crude extracts (2 mg of protein) were incubated with 5 $\mu$M SBFI plus the indicated concentrations of NaCl. The right hand group of tracings were recorded in the absence of any extract. The excitation intensity was scanned from 300 to 400 nm. B) For an assessment of the saturation fraction in the different extract samples, tracings as in (A) were done over a range of NaCl concentrations up to 200 mM so that the probe was fully saturated and gave maximum fluorescence. At each concentration, the ratio of illumination intensities at 340/385 nm (excitation) was calculated. Maximum fluorescence minus observed fluorescence/maximum fluorescence minus minimum fluorescence was plotted versus NaCl concentration.
Figure 4B:
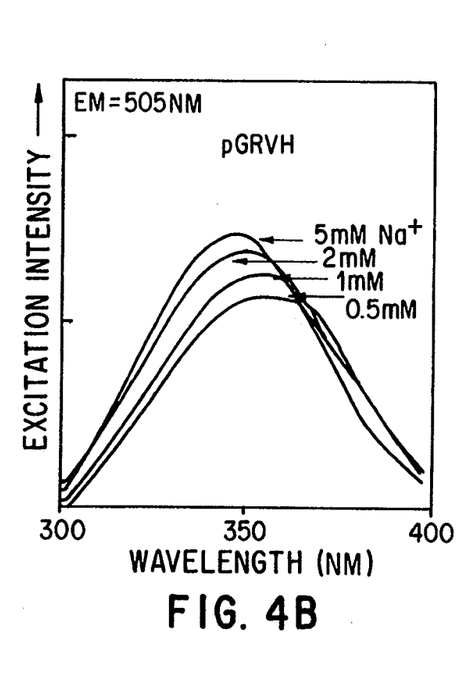
Figure 4C:
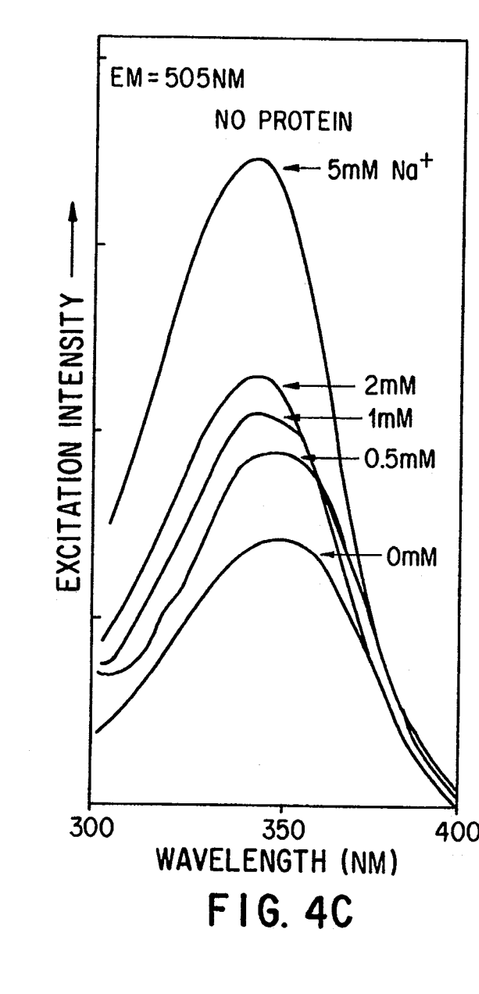
Figure 4D:
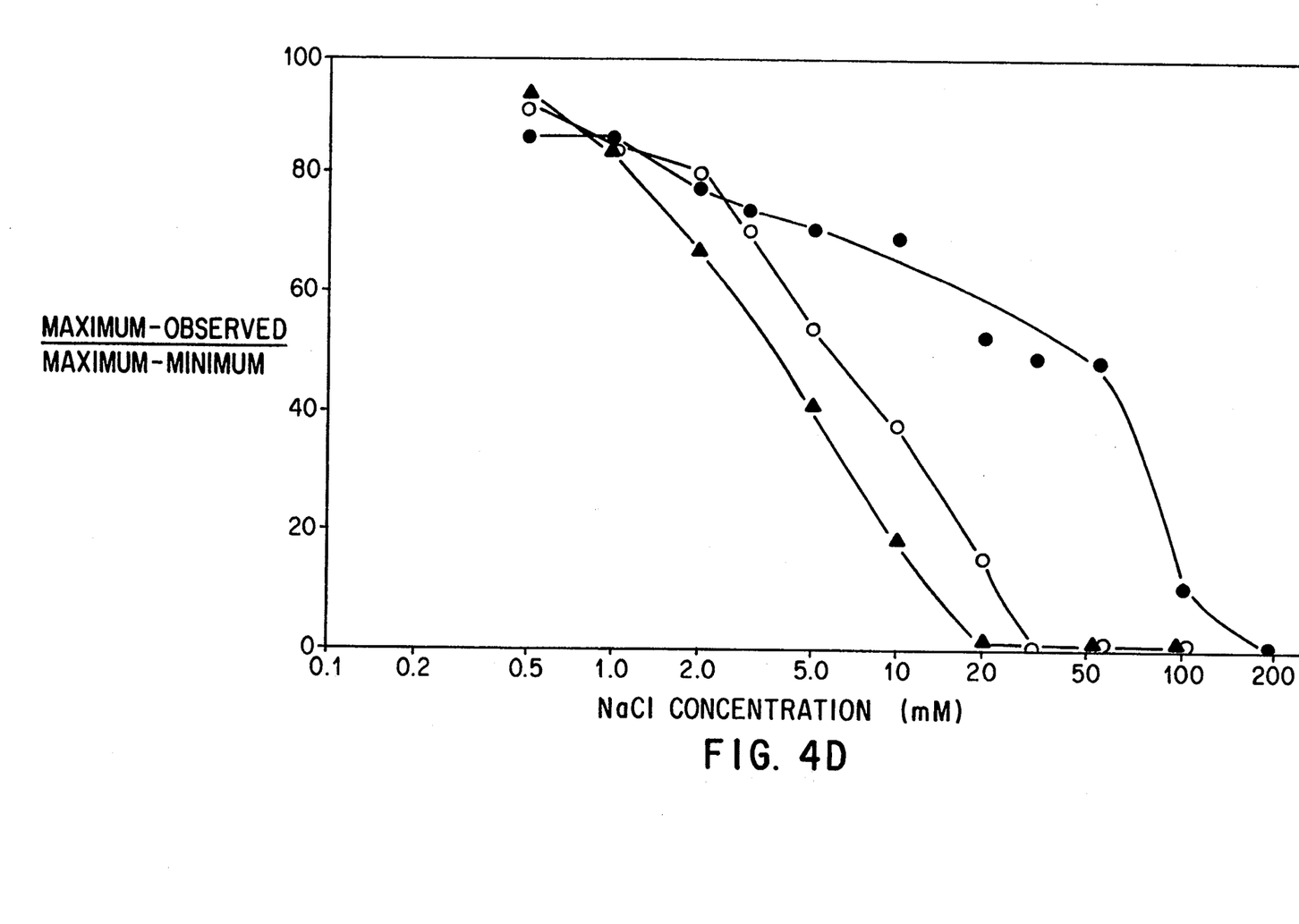

Although transformation of the double nha deletion of *E. coli* with pGRVH did not enhance the $Na^+/H^+$ activity of the membrane, it markedly enhanced the resistance of this strain to elevated concentrations of NaCl in the medium. In FIG. 3, growth of the following transformants of *E. coli* are compared on plating media of three different NaCl concentrations (0.2-0.4M) and 0.2M NaCl-containing medium at either pH 7.5 or pH 8.6: pGEM, the plasmid control; pGM36, a plasmid encoding the *E. coli* nhaA gene (Padan, E., Maisler, N., Taglicht, D., Karpel, R., & Schuldiner, S. (1989) *J. Biol. Chem.* 264, 20297-20302); pBE22, a plasmid containing the alkaliphile cadC gene (Ivey, D. M., Guffanti, A. A., Shen, A., Kudyan, N., & Krulwich, T. A. (1992) *J. Bacteriol.*, in press); and pGRVH. The pGRVH transformant grew almost as well as the double deletion strain that was transformed with the nhaA-encoding plasmid, at pH 7.5 and various NaCl concentrations; both of these transformants grew better than the transformant carrying the alkaliphile cadC gene and the transformant with the plasmid control did not grow at all. At 0.2M NaCl and elevated pH, only the pGRVH transformant of *E. coli* strain EP432 grew. Since this transformant had not shown enhanced antiport activity, and the deduced orf2 product suggested that it was unlikely to be an integral membrane antiporter, we considered the possibility that the orf2 product might be a $Na^+$-binding protein. Such a protein might enhance $Na^+/H^+$ antiport activity by somehow making the cytoplasmic substrate more available to the integral membrane antiporters; in the absence of $Na^+/H^+$ antiporters, enhanced NaCl resistance might be conferred by sequestration of the cytoplasmic NaCl while sluggish residual mechanisms, e.g. modest $Na^+/H^+$ antiport by other antiporters such as the $K^+/H^+$ antiporter, extrude the cation. As shown in FIG. 4, extracts of the EP432 transformant with pGRVH had significantly enhanced $Na^+$ binding activity relative to extracts from a control transformant. There was some variability from experiment to experiment in these crude extracts, but significant differences between control and transformant extracts were consistently observed in this concentration range of $Na^+$ and protein, and increased extract protein gave increased binding. The primary data shown in FIG. 4A were in the lower range of NaCl examined, where the differences were most pronounced. In order to better assess the binding capacity of the extract from the transformant vs. the control, several experiments were conducted over a broader range of NaCl concentrations such that saturation of the probe was achieved, and the saturation fraction could be calculated and plotted. Such a plot is shown in FIG. 4B.

The present invention is not to be limited in scope by the microorganisms deposited since the deposited embodiments are intended as illustrations of single aspects of the invention and any microorganisms which are functionally equivalent are within the scope of the invention.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. A purified and isolated DNA sequence selected from the group consisting of:
   (a) a DNA sequence encoding the NhaS amino acid sequence of FIG. 1 (SEQ. ID. NO.: 2);
   (b) a DNA sequence that hybridizes under stringent conditions to the complement of the nhaS DNA sequence of FIG. 1 (Seq. ID No.: 1), wherein the protein encoded by the coding strand of the DNA retains the sodium ion binding function of the NhaS protein; and
   (c) a DNA sequence that hybridizes under stringent conditions to the coding sequence of the nhaS DNA sequence of FIG. 1 (Seq. ID No.: 1), wherein the protein encoded by the coding strand of the DNA retains the sodium ion binding function of the NhaS protein.

2. A recombinant DNA vector containing the DNA sequence of claim 1.

3. A recombinant DNA vector containing the DNA sequence of claim 1, in which said DNA sequence is linked uninterrupted by stop codons, to a nucleotide sequence that encodes a peptide.

4. The purified and isolated DNA sequence of claim 1, wherein said DNA sequence encodes the NhaS amino acid sequence of FIG. 1 (SEQ. ID. NO.: 2).

5. The recombinant DNA vector of claim 2 in which the sequence is operatively associated with a regulatory sequence that controls gene expression in a host.

6. The recombinant DNA vector of claim 3 in which the nhaS sequence is operatively associated with a regulatory sequence that controls gene expression in a host.

7. An engineered host cell that contains the recombinant DNA vector of claim 5 or 6.

8. An engineered cell line that contains the recombinant DNA expression vector of claim 5 and expresses the nhaS.

9. An engineered cell line that contains the recombinant DNA expression vector of claim 6 and expresses the nhaS.

10. A method for producing recombinant NhaS, comprising:
    (a) culturing a host cell transformed with the recombinant DNA expression vector of claim 5 and which expresses the NhaS; and
    (b) recovering the NhaS gene product from the cell culture.

11. A method for producing recombinant nhaS, comprising:
    (a) culturing a host cell transformed with the recombinant DNA expression vector of claim 5 and which expresses the NhaS; and
    (b) recovering the NhaS gene product from the cell culture.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 572 base pairs
        ( B ) TYPE: nucleic acid
        ( C ) STRANDEDNESS: single
        ( D ) TOPOLOGY: unknown     ( i i ) MOLECULE TYPE: DNA (genomic)

( i x ) FEATURE:
        ( A ) NAME/KEY: CDS
        ( B ) LOCATION: 56..253

( x i ) SEQUENCE DESCRIPTION: SEQ ID NO:1:

```
AAACGTGGAT AAAGCAAGTG GATTTGATGC AAAGTAAGGA TAAGGAGGGA TGACC ATG        58
                                                              Met
                                                              1

TTT AGC CGT CTT ATC TCA ATT GTT AGT TTA ATC TTG TCT TTT TAC TTT       106
Phe Ser Arg Leu Ile Ser Ile Val Ser Leu Ile Leu Ser Phe Tyr Phe
          5                  10                  15

GCT TAC AAA TAT CGC TAC CGT GTT ATT AAT GCA GTG CTC GGA CGC CGT       154
Ala Tyr Lys Tyr Arg Tyr Arg Val Ile Asn Ala Val Leu Gly Arg Arg
        20                  25                  30

TGG CTG CGG AAA GTG ATT ATT GGT TTT GCG ATG CAG ATC CCG ATG ATC       202
Trp Leu Arg Lys Val Ile Ile Gly Phe Ala Met Gln Ile Pro Met Ile
        35                  40                  45

AGA GAC CGT ATG CTA GGA TCC GTT CTG CAG TCT AAT CGA CCT CAA AAT       250
Arg Asp Arg Met Leu Gly Ser Val Leu Gln Ser Asn Arg Pro Gln Asn
50                  55                  60                  65

GTG TAACAAACAA GAAAGTCTGA TGTTCACTTT AATGAAAGTT AAAGTATGGC            303
Val

ATCAGACTTT TTCGTATATA TACATACTAT AAGGCTTATT AATGTCCTAA CCTTTAGAGC     363

CCTTGTTATA CTATAAGGGA TAGGAGGATT GTATCTTGAA AGTGAAGTGG AGTACGATAT     423

GTTTTGATTT AGATAATACG TTATATAACC ATGAGTATGC TTTTAAGCGT GCGATTAAAC     483

AATGTTACTA TACAAAACTT CAGCAATGGA AGATATCCGT TGATCACGCT CCTCCATTTG     543

AAGCATGGTT TACTACATTT AAATATTAT                                      572
```

( 2 ) INFORMATION FOR SEQ ID NO:2:

( i ) SEQUENCE CHARACTERISTICS:
        ( A ) LENGTH: 66 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Phe Ser Arg Leu Ile Ser Ile Val Ser Leu Ile Leu Ser Phe Tyr
1               5                   10                  15

Phe Ala Tyr Lys Tyr Arg Tyr Arg Val Ile Asn Ala Val Leu Gly Arg
                20                  25                  30

Arg Trp Leu Arg Lys Val Ile Ile Gly Phe Ala Met Gln Ile Pro Met
            35                  40                  45

Ile Arg Asp Arg Met Leu Gly Ser Val Leu Gln Ser Asn Arg Pro Gln
    50                  55                  60
```

Asn Val
65